United States Patent [19]

Eifert et al.

[11] Patent Number: 4,596,893
[45] Date of Patent: Jun. 24, 1986

[54] 2-TRIFLUOROMETHYL-4,6-DINITRO-PHENOL AND DERIVATIVES THEREOF, PROCESS FOR THE PREPARATION THEREOF AND HERBICIDAL, ACARICIDAL AND CROP REGULATION COMPOSITIONS CONTAINING SAME

[75] Inventors: Gyula Eifert, Dunaharaszti; Ferenc Bihari, Budapest; István Magyari, Gödöllö; Jenö Mészáros, Budapest; Péter Inczédy, Budapest; Judit Timár, Budapest; Rudolf Czövek, Budapest; Péter Bohus, Budapest; Egon Klumpp, Budapest; Erzsébet Schüszler, Budapest, all of Hungary

[73] Assignee: Budapesti Vegyimüvek, Budapest, Hungary

[21] Appl. No.: 737,574

[22] Filed: May 23, 1985

Related U.S. Application Data

[63] Continuation of Ser. No. 575,857, Jan. 31, 1984, abandoned.

[51] Int. Cl.$^4$ .............................................. C07C 79/32
[52] U.S. Cl. .................................................. 568/709
[58] Field of Search ......................................... 568/709

[56] References Cited

U.S. PATENT DOCUMENTS 3,813,446  5/1974  Jacobs ............................... 568/709
3,943,180  3/1976  Wagner .............................. 568/709

FOREIGN PATENT DOCUMENTS 2001570  7/1971  Fed. Rep. of Germany ...... 568/709

OTHER PUBLICATIONS

Millot et al., "Chemical Abstracts", vol. 82 (1975) p. 124,324w.
Olah, "J. Org. Chem.", vol. 41(21) (1976) pp. 3448-3451.
Yogupól'ski et al, "Chemical Abstracts", vol. 49, (1955) pp. 8866-8867.
Koho, "Chemical Abstracts", vol. 94, (1981) p. 121,089k.

*Primary Examiner*—Werren B. Lone
*Attorney, Agent, or Firm*—Gabriel P. Katona

[57] ABSTRACT

The present invention relates to 2-trifluoro-methyl-4,6-dinitro-phenol and derivatives thereof prepared by hydrolyzing 2-chloro-3,5-dinitrobenzotrifluoride with an alkali hydroxide or alkaline earth metal hydroxide at elevated temperature in an aqueous medium without catalyst, 2-trifluoro-methyl-4,6-dinitro-phenol show herbicidal, acaricidal and crop regulating properties.

7 Claims, No Drawings

2-TRIFLUOROMETHYL-4,6-DINITRO-PHENOL AND DERIVATIVES THEREOF, PROCESS FOR THE PREPARATION THEREOF AND HERBICIDAL, ACARICIDAL AND CROP REGULATION COMPOSITIONS CONTAINING SAME

This is a continuing application of application Ser. No. 575,857, filed on Jan. 31, 1984, now abandoned.

The present invention relates to new 2-trifluoromethyl-4,6-dinitro-phenol and derivatives thereof, herbicidal, acaricidal and crop regulating compositions containing same as active ingredient and process for the preparation of the compounds.

The new 2-trifluoromethyl-4,6-dinitro-phenol and derivatives thereof can be characterized by the general formula I

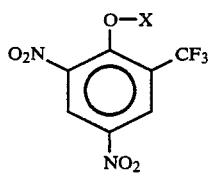  /I/ wherein X stands for hydrogen, alkali metal, alkali earth metal, $C_{1-10}$ alkoxyalkyl, or alkenylcarbonyl, phenylcarbonyl, halogen-substituted phenylcarbonyl, or a group of the general formula /a/

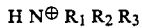 /a/ wherein $R_1$, $R_2$ and $R_3$ are the same or different and stand for hydrogen, alkyl, alkoxyalkyl, alkenyl, hydroxyalkyl, cycloalkyl, phenyl or substituted phenyl.

The alkyl moiety of the alkoxyalkyl substituent can be straight or branched chain alkyl having 1–10 carbon atoms; preferably 1–4 carbon atoms, such as, for example, methyl, ethyl, propyl and butyl. The alkenyl moiety of the alkenyl substituent having 2–10 carbon atoms, can be straight or branched chain alkenyl having 2–10 carbon atoms; preferably 2–4 carbon atoms, such as, for example, vinyl, isopropenyl, ethylene, propylene and butylene. The halogen-substituted phenylcarbonyl refers to phenyl substituted by chloro, bromo or iodo moieties; preferably by chloro, for example, 2-chlorophenylcarbonyl and 4-chlorophenylcarbonyl.

The alkyl moiety means a straight or branched chain alkyl substituent having 1–4 carbon atoms, such as for example, methyl, ethyl, n-propyl, isopropyl, n-butyl, isobutyl, tert-butyl and sec-butyl. The alkoxyalkyl moiety referes to a straight chain of 3–5 carbon atoms, for example, methoxyethyl, etyhoxyethyl. The alkenyl refers to a straight or branched chain having 1–6 carbon atoms; preferably 1–4, for example, ethylene, propylene, butylene and 2-methylallyl.

The compounds of the general formula I show herbicidal and acaricidal and crop regulating activity.

The compounds can be formulated to herbicidal, acaricidal or crop regulating compositions, which preferably contain 0.1 to 80% by weight of active ingredient and the usual carriers and excipients.

The compositions may be prepared in the form of emulsifiable concentrates, aqueous suspensions, spray in the form of dust, oily paste, granulates, etc.

The present invention further provides a process for the preparation of the compounds of the general formula I by alkaline hydrolysis of 2-chloro-3,5-dinitro-benzotrifluoride in aqueous medium without catalyst, and if desired followed by the conversion of the obtained phenolate to the end product by method known per se.

The structurally similar 2-methyl-4,6-dinitro-phenol, i.e. the so called dinitro-ortho-cresol /DNOC/ and alkali metal salts thereof are known to show herbicidal and acaricidal activity.

Known compositions containing such active ingredients are Novenda and Krezonit. Similarly 2-sec.-butyl-4,6-dinitro-phenol /DNBP/ of similar chemical structure is a known herbicide, used at smaller dosis as biostimulator in corn cultures /Ohlrogge, A.J.: The Development of DNBP /Dinoseb/ as a Biostimulant for Corn in Plant Growth Regulators, editor: Stutte, C.A. 79–87 pp. Advances in chemistry series, 159. American Chemical Society, Washington, 1977./ No technical reference could be found concerning the preparation or biological activity of the compounds of the general formula I according to the invention only for similar compounds. In GB PS No. 1 378 994 the preparation of 2,4-bis-/trifluoromethyl/-6-nitro-phenol and derivatives thereof is disclosed. In U.S. Pat. No. 3,813,446 the preparation of 2,6-dinitro-4-trifluoromethyl-phenol and derivatives thereof is described. The known processes are performed in an organic solvent, optionally in the presence of phasis transfer catalysts. In said processes undesired side-reactions take place, such as ether derivative formation in methanol or hydrolysis of the trifluoromethyl group into carboxylic group. According to the present invention no such side reactions occur.

The process of the invention is suitable for the preparation of the compounds of the general formula I at industrial scale economically and in pure state.

We have also found that the new compounds show a surprisingly good biological activity. After subjecting the various compositions of the invention containing the new compounds as active ingredient we have found that new herbicidal, acaricidal and crop regulating compositions were obtained.

When preparing the compounds of the general formula I - wherein X stands for hydrogen, alkali metal, alkali earth metal, $C_{1-20}$ alkylcarbonyl, or alkenylcarbonyl, phenylcarbonyl, halogen-substituted phenylcarbonyl, or a group of the general formula /a/, wherein $R_1$, $R_2$ and $R_3$ are the same or different and stand for hydrogen, alkyl, alkoxyalkyl, alkenyl, hydroxyalkyl, cycloalkyl, phenyl or substituted phenyl - one may proceed by first preparing an alkali metal or alkali earth metal phenolate by reacting 2-chloro-3,5-dinitro-benzotrifluoride with alkali metal or alkali earth metal hydroxide. The reaction is conducted in an aqueous medium without catalyst at 20°–100° C., preferably at 60°–80° C. at an alkali concentration of 5 to 20% by weight preferably 10 to 15% by weight. The phenolate formed during the alkaline hydrolysis is, if desired, converted to phenol with an acid by method known per se. The phenol is, if desired, converted to a phenolate derivative by using a base corresponding to the substituents of the general formula I latter being used as pesticidal active ingredient after isolation from the mixture.

The pesticidal composition is prepared by using the conventionally used carriers and excipients. The active ingredient content can vary within a range of 0.1 to 80% by weight depending on the formulation type and method of application. The composition is used as herbicide, acaricide or crop regulating agent.

The process of the invention is simple, economical and reproduceable and suitable for the preparation of the new compounds of the invention which broaden the selection of pesticide agents due to their bioactivity.

The details of the invention are illustrated by the following Examples which serve merely for illustration and not for limitation. Preparation of the compounds of the general formula I.

EXAMPLE 1

To a 1000 cm³ flask equipped with a stirrer, dropping funnel, reflux and thermometer 300 g /0.75 mole/ of a 10% by weight NaOH solution are added 81.3 g /0.3 mole/ of 2-chloro-3,5-dinitro-benzotrifluoride of a purity of 95% are added under stirring. The temperature is raised to 60° C. and the reaction mixture is stirred at 60°–65° C. for 4 hours, while the aqueous suspension forms an emulsion. The reaction mixture is then cooled to room temperature /20°–25° C./ under stirring and within 1 hour a 37% hydrochloric acid solution corresponding to 0.82 mole HCl is added in equal portions under vigorous stirring. The precipitated product is filtered, washed with water and dried to constant weight at room temperature. 2-Trifluoromethyl-4,6-dinitro-phenol is obtained /68.1 g., purity: 94%/ Idenfication was carried out by a mass spectrometer connected to a gas chromatograph.

Yield: 90%.

EXAMPLE 2

To 250 l enamelled reactor equipped with a mixer, and reflux 60 kg. of water are added and under stirring 32.5 kg. of 2-chloro-3,5-dinitro-benzotrifluoride are added through a powder funnel. The reaction mixture is heated to 75° C. and at equal rate 65 kg. of a 20% NaOH solution are pumped in while the temperature is maintained at 75°–80° C. The reaction mixture is stirred at 75°–80° C. for 3.5 hours. The reaction mixture is cooled to room temperature and within 1 hour 9.5 cc. HCl are added at equal rate. The precipitated product is centrifuged, washed with water and dried at room temperature to constant weight. The obtained product is 2-trifluoromethyl-4,6-dinitro-phenol, /28 kg./.

Purity: 94.3%, yield: 92.4%.

Preparation of the composition

EXAMPLE 3

60% By Weight Emulsifiable Concentrate /EC/

433 g. of 97% 2-trifluoromethyl-4,6-dinitro-phenol are dissolved at 40° C. in a mixture of 200 g. of isophoron and 25 g. of xylene. The solution is cooled to room temperature and filtered through 0.1 micrometer GAF filter. To the filtrate 36 g of Tensiofix B 7425 and 6 g. of Tensiofix LS emulsifier are added under stirring.

EXAMPLE 4

60% By Weight of Emulsifiable Concentrate /EC/

One proceeds as disclosed in Example 3 but isophoron is replaced by cyclohexanone and xylene is replaced by aromatol solvent and the following emulsifying agents are used:

|  | A | B | C |
|---|---|---|---|
| Tensiofix AS g. | 18 | — | 10 |

-continued

|  | A | B | C |
|---|---|---|---|
| Tensiofix LS g. | 24 | — | — |
| Emulsogen EL g. | — | 12 | 25 |
| Sapoegenat T 180 g. | — | 10 | — |
| Sapoegenat T 500 g. | — | 20 | 7 |

EXAMPLE 5

20% By Weight of Water Soluble Concentrate /WSC/

To 300 g. of a 30% by weight of 2-trifluoromethyl-4,6-dinitro-phenol-Na aqueous solution 50 g. ethylene glycol and 4 g. of Tensiofix CG-21 emulsifiers are added. The solution is supplemented to 450 g. with ionexchanged water under stirring.

EXAMPLE 6

20% By Weight of Oily Paste 620 g. of 97% 2-trifluoromethyl-4,6-dinitro-phenol are dissolved in 500 g. of cyclohexanone and to this solution 120 g. of cosmetic vaseline oil are poured. The obtained solution is emulsified with a 10% solution of Tensiofix PO-132 emulsifier by means of Ultra-turrax mixer while the temperature is maintained at 30° C. After cooling to 15° C. 50 g. of 0.2% by weight of Kelsan S-ethylene glycol solution is dispersed in the mixture within 1 hours under slow stirring.

EXAMPLE 7

Herbicide Activity Test in Green House

In culture dishes white mustard, pig weed, fat hen, autumn wheat, Italian grass and corn seeds were sown. When the seeds were sprouted 10% EC and 10% WSC were prepared from the compounds to be tested, and after dilution with water 0.2% spray was prepared. 2–4 leaves plants were sprayed with this liquid so that for each compound a dose corresponding to 2.5–5–10 kg./ha active ingredient was used. On the 14th day after the treatment the extent of the injury of the plants was evaluated and expressed in %. The results are summarized in Table 1.

TABLE 1

| Compound | Dose kg/ha | white mustard | pig weed | fat hen | Italian grass | autumn wheat | corn |
|---|---|---|---|---|---|---|---|
| 2-trifluoro- | 1.25 | 45 | 50 | 75 | 0 | 0 | 0 |
| methyl- | 2.55 | 75 | 85 | 90 | 10 | 5 | 5 |
| 4,6-dinitro-phenol | 5.0 | 95 | 100 | 100 | 30 | 10 | 15 |
| 2-trifluoro- | 1.25 | 40 | 50 | 70 | 0 | 0 | 0 |
| methyl- | 2.5 | 60 | 60 | 75 | — | — | — |
| 4,6-dinitro-phenol-diethanolamine | 5.0 | 80 | 85 | 80 | 10 | 10 | 10 |
| 2-trifluoro- | 1.25 | 45 | 50 | 70 | 0 | 0 | 0 |
| methyl- | 2.5 | 55 | 65 | 75 | 0 | 0 | 0 |
| 4,6-dinitro-phenol-dimethylamine | 5.0 | 75 | 80 | 85 | 20 | 10 | 10 |
| 2-trifluoro- | 1.25 | 50 | 60 | 70 | 0 | 0 | 0 |
| methyl- | 2.5 | 80 | 85 | 90 | 10 | 0 | 10 |
| 4,6-dinitro-phenol-Na | 5.0 | 100 | 100 | 100 | 15 | 15 | 15 |
| 2-trifluoro- | 1.25 | 65 | 45 | 70 | 0 | 0 | 0 |
| methyl- | 2.5 | 75 | 85 | 90 | 10 | 0 | 10 |
| 4,6-dinitro-phenol-K | 5.0 | 90 | 100 | 100 | 15 | 15 | 15 |
| 2-trifluoro- | 1.25 | 40 | 50 | 70 | 0 | 0 | 0 |

TABLE 1-continued

| Compound | Dose kg/ha | white mustard | pig weed | fat hen | Italian grass | autumn wheat | corn |
|---|---|---|---|---|---|---|---|
| methyl-4,6-dinitro-phenol-methyl carbonyl | 2.5 | 70 | 80 | 90 | 10 | 0 | 0 |
| | 5.0 | 90 | 95 | 100 | 20 | 10 | 10 |
| 2-trifluoro-methyl-4,6-dinitro-phenol-ethyl carbonyl | 1.25 | 40 | 40 | 60 | 0 | 0 | 0 |
| | 2.5 | 50 | 60 | 70 | 0 | 0 | 0 |
| | 5.0 | 80 | 80 | 80 | 10 | 10 | 10 |

EXAMPLE 8

Determination of Hill-Reaction Inhibition

By means of the method of Arnon et al. spinach chloroplastises were isolated. To 1 g. of leaves freed from the ribs 6 ml. of a 0.35 molar solution of NaCl and 0.6 ml. of 0.2 molar TRIS-buffer were added, the mixture was ground, and the homogenizate was filtered through a gauze of several layers and centrifuged for 5 minutes at a rate of 2000 rotations. The chloroplastis precipitate was suspended in a 0.035 molar NaCl, homogenized in a Potter tube and the thus obtained chloroplastis suspension was held at 0° C. until use. A reaction mixture of the chloroplastis suspension $K_3Fe/CN/_6$, $K_2HPO_4$, TRIS.HCl buffer, $MgCl_2$ of suitable concentration and ratio and a solution of the compounds of the general formula /I/ as inhibitors and N-/3,4-dichloro-phenyl/-N',N'-dimethyl-urea /DCMU/ and dinitro-ortho-cresol /DNOC/ as standards of a molar concentration of $1 \times 10^{-10} - 1 \times 10^{-3}$ were subjected to an exposure of 5000 lux light intensity for 20 minutes whereafter the reaction was quenched with 25% trichloroacetic acid solution /TCA/. The precipitate was removed by centrifuging and the extinction of the solution was measured at 420 nm, with a photometer of type Spektromom 204. The measuring series was conducted also with reaction mixtures held in the dark. Hill-reaction inhibition was determined on the basis of the extinction differences measured in dark and light reactions and converted to /μg/ml potassium ferricyanide concentration on the basis of calibration curve. The % values of the inhibition are plotted against concentration and concentrations belonging to 50% inhibition were read from this curve /$I_{50}$/.

Results are shown in Table 2.

TABLE 2

| Compound | $I_{50}$ micromole/$dm^3$ |
|---|---|
| 2-trifluoromethyl-4,6-dinitro-phenol | 0.21 |
| 2-trifluoromethyl-4,6-dinitro-phenol-diethanol-amine | 0.57 |
| 2-trifluoromethyl-4,6-dinitro-phenol-dimethyl-amine | 0.52 |
| 2-trifluoromethyl-4,6-dinitro-phenol-NH$_4$ | 0.25 |
| 2-trifluoromethyl-4,6-dinitro-phenol-Na | 0.20 |
| 2-trifluoromethyl-4,6-dinitro-phenol-K | 0.31 |
| dinitro-orthro-cresol-Na standard | 0.86 |
| N—/3,4-dichloro-phenyl/-N',N'— | 0.071 |

TABLE 2-continued

| Compound | $I_{50}$ micromole/$dm^3$ |
|---|---|
| dimethyl urea | |

One can see that 2-trifluoromethyl-4,6-dinitro-phenol and salts thereof are similarly to N-/3,4-dichloro-phenyl/-N',N'-dimethyl-urea inhibitors of the 2. photochemical system and their effectivity is in between the effectivity of N-/3,4-dichloro-phenyl/-N',N'-dimethyl-urea and dinitro-ortho-cresol. Among the 2-trifluoromethyl-4,6-dinitro-phenol compounds the amine salts are less effective than the alkali and ammonium salts.

EXAMPLE 9

Herbicide Test in Corn Field

The test was carried out with 2-trifluoromethyl-4,6-dinitro-phenol-Na 20 WSC formulated according to Example 5 and with 2-trifluoromethyl-4,6-dinitro-phenol 60 EC formulated according to Example 3. The test was performed on a brown forest soil containing 1.8% of organic substance. The soil was seeded on April 25th and 26th with corn of type Pioneer 3950 with a germ number of 73000/ha to a depth of 8 to 10 cm. Spraying was conducted on May 30th at 1.5 atm. by means of a parcel spraying machine equipped with a sprinkler of type Tee-Jet 11002 with water at a rate of 300 liter/ha. At this time the corn had 3–4 leaves, the main part of the weeds had 2–4 leaves. The tests were repeated 4 times. At spraying the field was covered with weeds in 87.5%, in 58% with pig weed, in 27% with fat hen and the residue was covered with barnyard grass. The activity was evaluated on June 15th. The weed killing activity and the phytotoxic symptoms observed in corn were evaluated by EWRC scale.

The EWRC scale needed for evaluation is contained in Table 3 and the results are summarized in Table 4. Data in Table 4 are average values obtained from 4 repetitions.

TABLE 3

| | EWRC value scale | | | |
|---|---|---|---|---|
| Value scale: | Weed killing effect | Killing % | Effect on domesticated plants | |
| | | | injury | killing % |
| 1. | excellent | 100 | no | 0 |
| 2. | excellent | 99 | very slight | 1 |
| 3. | good | 98 | slight | 2 |
| 4. | satisfactory | 95 | slightly moderate | 5 |
| 5. | sufficient | 90 | moderate | 10 |
| 6. | insufficient | 75 | average | 25 |
| 7. | bad | 50 | strong | 50 |
| 8 | very bad | 25 | very strong | 75 |
| 9. | unsuitable | 0 | complete killing | 100 |

TABLE 4

| | | EWRC values | | | |
|---|---|---|---|---|---|
| Composition | Dose l/ha | pig weed | fat hen | Barnyard grass | corn |
| 2-trifluoromethyl-4,6-dinitro-phenol-Na 20 WSC | 5 | 3 | 2 | 5 | 1.5 |
| | 10 | 1.5 | 1 | 2 | 1.5 |
| 2-trifluoromethyl-4,6-dinitro-phenol 60 EC | 1.6 | 4 | 3.5 | 7 | 1 |
| | 3.2 | 2 | 1 | 3.5 | 1 |

EXAMPLE 10

Crop Regulation of Corn

Test compound: 2-Trifluoromethyl-4,6-dinitro-phenol-Na 20% WSC

Corn of the type MVSC 3780 with a germ number of 55000/ha was seeded on April 20th. Spraying from helicopter was carried out on July 22nd at the beginning of the blooming of the corn at a beard length of 4–5 cm. Application rate 0.25 liter/ha -(0.05 kg./ha active ingredient). The lands of parcels were 4 ha and the test was repeated twice. For each ha 50 liters of water was used. Corn was harvested on November 3rd. Results are summarized in Table 5.

TABLE 5

|   | length of corn-ear cm | length of corn-ear covered by grains cm | weight of corn-ear dkg |
|---|---|---|---|
| 1. repetition | 16.07 ± 2.19 62% of the ears is defective | 14.52 ± 2.80 90.35% of the corn-ear length is covered by grain | 22.96 ± 6 |
| 2. repetition | 17.06 ± 2.71 66% of the ears is defective | 15.35 ± 3.93 93.34% of the ears is covered by grain | 20.84 ± 5 |
| ∅ control | 17.33 ± 1.87 84% of the corn-ears is defective | 15.33 ± 2.48 89.97% of the ears is covered by grain | 19.16 ± 4 |

Crop averages:
1. repetition: 4.25 to/ha = 119.7%
2. repetition: 4.08 to/ha = 114.9%
∅ control: 3.55 to/ha = 100%.

According to the test 2-trifluoromethyl-4,6-dinitro-phenol-Na 20WSC could induce a significant crop increase due to its effect on the increase of the grain-size and on the better grain-density.

EXAMPLE 11

Acaricide Activity Test

The test was adjusted on apples of Golden delicious type planted in a 7.5 m×4.5 m field in parcels of 5 trees arranged in rows. Spraying was carried out on March 16th before budding at a pressure of 20 bar by a manual high pressure spraying gun of Haflinger spraying car. Test-compounds: 2-trifluoromethyl-4,6-dinitro-phenol-Na 20% WSC and 2-trifluoromethyl-4,6-dinitro-phenol 60% EC. Protective activity against eggs of spider mite living through the winter was evaluated by collecting 5×10 pieces of fruit-buds from the treated and untreated parcels 48 hours after the treatment. Observations were continued in the laboratory until the mite hatching terminated /12 days/. Mortality % was determined on the basis of the number of the hatched mites and expressed in the % of the control. Results are shown in Table 6.

TABLE 6

| Composition | Concentration of the composition in the spray liquid % | number of hatched mites in 5 × 10 fruitbuds pieces | egg mortality % | infection in % of the control |
|---|---|---|---|---|
| 2-trifluoromethyl-4,6-dinitro-phenol-Na 20 WSC | 2.5 | 19 | 96.35 | 3.65 |
| 2-trifluoromethyl-4,6-dinitro-phenol 60 EC | 0.8 | 23 | 95.59 | 4.41 |
| Dinitro-ortho-cresol/DNOC-25/paste | 2.0 | 27 | 94.82 | 5.18 |
| Untreated control | — | 521 | 0 | 100 |

EXAMPLE 12

Into a flask of 4000 milliliters equipped with a stirrer, dropping funnel, reflux and thermometer 1008.9 g (4 moles) of 2-hydroxy-3,5-dinitro-benzotrifluoride and 2000 ml. acetonitrile are added and under cooling at 20–30 degrees centigrade 312.8 g (4 moles) of acetyl chloride are added. After the addition is completed, the mixture is stirred for a further hour, the solution is neutralized with triethylamine and the triethylamine hydrochloride is filtered off. Acetonitrile is then removed under vacuum, and the residue is poured into water under cooling and stirring. The precipitated crystals are filtered, washed with ethanol and dried. 2-trifluoromethyl-4,6-dinitrophenol methyl carbonyl is obtained. Yield 98%, purity 98%.

Compounds of the general formula I achieved the activity of Novenda-25 paste containing dinitro-ortho-cresol.

We claim:

1. 2-Trifluoromethyl-4,6-dinitro-phenol derivatives thereof having the general formula

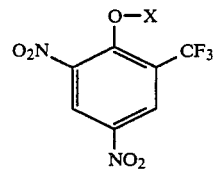

(I)

wherein X is alkali metal, alkali earth metal, alkylcarbonyl or alkenylcarbonyl having 1–10 carbon atoms phenylcarbonyl, or halogen-substituted phenylcarbonyl, or a group having the general formula

(a)

wherein $R_1$ $R_2$ and $R_3$ can be independently of each other hydrogen alkyl, alkoxyalkyl, alkenyl, hydroxyalkyl, cycloalkyl, phenyl, or substituted phenyl.

2. Herbicidal, acaricidal or crop regulating composition comprising as active ingredient a compound of the formula

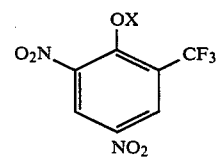

II wherein X is halogen, alkali metal, alkaline earth metal, alkylcarbonyl of 1–10 carbon atoms, phenylcarbonyl, or a group having the formula $$H \overset{\oplus}{N} R_1 R_2 R_3$$

wherein $R_1$, $R_2$, and $R_3$ can independently of each other be hydrogen, alkyl, alkoxyalkyl, alkenyl, hydroxyalkyl, cycloalkyl, phenyl or substituted phenyl.

3. Process for the preparation of 2-trifluoromethyl-4,6-dinitrophenol and derivatives thereof of the formula II

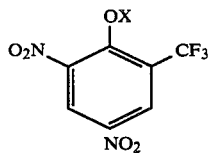

wherein X is halogen, alkali metal, alkaline earth metal, alkylcarbonyl of 1–10 carbon atoms, phenylcarbonyl, or halogen-substituted phenylcarbonyl, or a group having the formula $$H \overset{\oplus}{N} R_1 R_2 R_3$$

wherein $R_1$, $R_2$, and $R_3$ can independently of each other by hydrogen, alkyl, alkoxyalkyl, alkenyl, hydroxyalkyl, cycloalkyl, phenyl or substituted phenyl, which comprises hydrolyzing at from about 2 to about 100 degrees centigrade 2-chloro-3,5-dinitrobenzotrifluoride with an alkali hydroxide or alkaline earth metal hydroxide in an aqueous medium without catalyst, and recovering the obtained phenolate.

4. Process as claimed in claim 1, which comprises conducting the hydrolysis at an alkali concentration of 5 to 20% by weight.

5. Process as claimed in claim 1 which comprises performing the hydrolysis at 60°–80° C.

6. Process as claimed in claim 4, which comprises conducting the hydrolysis at an alkali concentration of from about 10 to about 15% by weight.

7. Process as claimed in claim 3, further comprising converting the obtained phenolate into phenol, or into a derivative according to formula II.

* * * * *